United States Patent

Gardiner et al.

[11] 4,022,912
[45] May 10, 1977

[54] USE OF 1-DECARBOXY-1-HYDROXYMETHYL-PGE$_1$ IN THERAPEUTIC BRONCHODILATION

[75] Inventors: Phillip J. Gardiner, Maidenhead; Cyril Schneider, Whitton Twickenham, both of England

[73] Assignee: Miles Laboratories, Inc., Elkhart, Ind.

[22] Filed: Feb. 9, 1976

[21] Appl. No.: 656,159

[52] U.S. Cl. .............................................. 424/331
[51] Int. Cl.$^2$ ...................................... A61K 31/12
[58] Field of Search ................................... 424/331

[56] References Cited

UNITED STATES PATENTS 3,636,120  1/1972  Pike .............................. 260/586 R

*Primary Examiner*—Sam Rosen
*Attorney, Agent, or Firm*—Myron B. Sokolowski

[57] ABSTRACT

Administration of a therapeutically effective dose of 15(S)-1,11α,15α-trihydroxy-9-oxo-13-trans-prostene (1-decarboxy-1-hydroxymethyl-PGE$_1$) produces bronchodilation in an individual in whom that therapy is indicated.

3 Claims, No Drawings

USE OF 1-DECARBOXY-1-HYDROXYMETHYL-PGE$_1$ IN THERAPEUTIC BRONCHODILATION

BACKGROUND OF THE INVENTION

1. Field

This invention generally pertains to chemotherapeutic methods of causing bronchodilation in individuals having respiratory disorders such as emphysema, intrinsic or allergic asthma, or other related diseases. The invention specifically comprises a new therapeutic use of 15(S)-1,11α,15α-trihydroxy-9-oxo-13-trans-prostene as a bronchodilating agent.

2. Prior Art

A. 1-Decarboxy-1-Hydroxymethyl-PGE$_1$

U.S. Pat. No. 3,636,120 (1/72; "Pike") discloses 1-decarboxy-1-hydroxymethyl derivatives of PGE$_1$ that have the common structure,

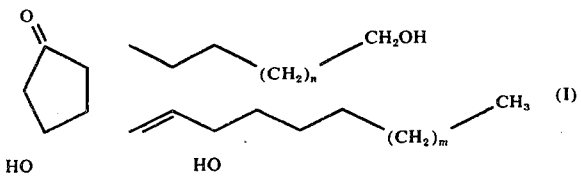

In I, $m$ and $n$ are integers of the respective sets 0-2 and 2-5. Pike in particular describes 15(S)-1,11α,15α-trihydroxy-9-oxo-13-trans-prostene (1-decarboxy-1-hydroxymethyl-PGE$_1$),

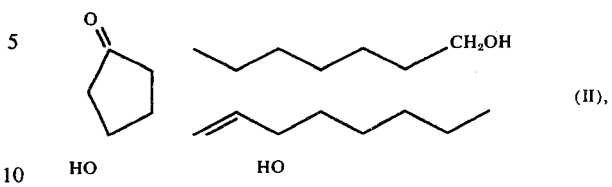

and a method for its synthesis.

Synthesis of II consists of the following sequence of reactions:

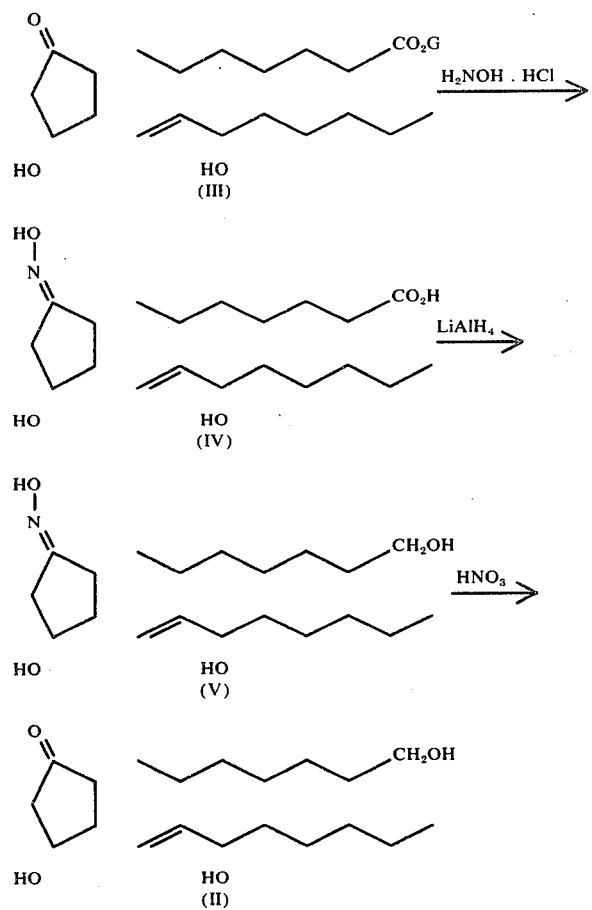

In the preceding synthetic pathway, reaction of PGE$_1$, III, with hydroxylamine hydrochloride and sodium acetate in aqueous methanol at room temperature for 18 hours yields the 9-oxime of 9-dihydro-PGE$_1$, IV. Reduction of IV (dissolved in tetrahydrofuran) with lithium aluminum hydride in ether for 2 hours under nitrogen atmosphere at room temperature gives the 1-hydroxymethyl-9-oxime of PGE$_1$, V. Treatment of V with nitrous acid in ether first at 10° C for 1 hour and then at room temperature for 0.5 hour converts V to 1-decarboxy-1-hydroxymethyl-PGE$_1$, II.

Pike teaches that II antagonizes mobilization of free fatty acids induced by epinephrine and proposes that II may have utility in studies of diseases involving abnormal mobilization of lipids (e.g. vascular diseases, diabetes mellitus, or hyperthyroidism). Pike further discloses that II inhibits platelet aggregation and suggests that the compound should be useful in studies on thrombogenesis, which studies may lead to an understanding of pathologies such as atherosclerosis, post-operative venous thrombo-embolism, and myocardial infarcts. The net teaching of Pike in that regard, thereof, is that the compound is an excellent tool in experimental physiology.

The only therapeutic utility of 1-decarboxy-1-hydroxymethyl-$PGE_1$ described in Pike is that the compound is a nasal decongestant. The proposed dose ranges for human use is from 10 $\mu$g ml$^{-1}$ to 10 mg ml$^{-1}$ in a pharmacologically acceptable topical vehicle.

Pike neither expressly nor implicitly refers to use of 1-decarboxy-1-hydroxymethyl-$PGE_1$ in a therapeutic method of producing bronchodilation either in man or in an experimental animal.

B. Prostaglandin $E_1$

Prostaglandin $E_1$ ($PGE_1$; 11$\alpha$,15$\alpha$-dihydroxy-9-oxo-13-trans-prostenoic acid) relaxes tracheal smooth muscle isolated from a guinea pig or from a human (Main, Brit. J. Pharmacol. Chemother., 22: 511 [1964]; Sweatman and Collier, Nature, 217: 69 [1968]).

$PGE_1$ also relaxes bronchial smooth muscle in vivo when administered by inhalation or intravenously. Intravenous injection of $PGE_1$ in humans causes an increase in total and alveolar ventilation but produces concomitant untoward side effects of general discomfort, headache, and nausea (Carlson, et al., Acta Physiol. Scand. 75: 161 [1969]). Inhalational administration of $PGE_1$ to guinea pigs produces bronchodilation that is superior to that induced by isoprenaline (Large, et al., Nature, 224: 78 [1969]); however, $PGE_1$ either as the free acid or in salt form, consistently elicits coughing in individuals when administered by inhalation (Cuthbert, Brit. Med. J., 4: 723 [1969]; Herxheimer and Roetscher, Europ. J. Clin. Pharmacol., 3: 123 [1971]; and Cuthbert, Proc. Roy. Soc. Med., 64: 15 [1971]).

The combined teaching of the cited prior art leads away from the present invention. Pike contains no disclosure, either expressed or implied, that directs a skilled person in the field to the claimed new use of 1-decarboxy-1-hydroxymethyl-$PGE_1$; moreover the prior art on the bronchodilating properties of $PGE_1$ discourages experimentation with 1-decarboxy-1-hydroxymethyl-$PGE_1$ in the field. The unexpected discoveries that the latter compound is 24-times more potent than $PGE_1$ at 0.001 $\mu$g/ml in relaxing guinea pig tracheal tissue that 1-decarboxy-1-methylhydroxy-$PGE_1$ antagonizes the effects of $PGE_1$ in the guinea pig ileum and that 1-decarboxy-1-methylhydroxy-$PGE_1$ is less irritating than $PGE_1$ demonstrate the nonobvious new use of 1-decarboxy-1-hydroxymethyl-$PGE_1$ as a bronchodilator.

DESCRIPTION OF THE INVENTION

The subject matter of this invention is a new use of 1-decarboxy-1-hydroxymethyl-$PGE_1$ in a method of causing bronchodilation by administering a therapeutically effective amount of compound to an individual in whom that therapy is indicated. In the preceding sentence as well as elsewhere in this specification, "individual" means a human being or a laboratory animal used as an experimental model thereof. "Therapeutically effective amount" means a dosage or a series of dosages that is effective in producing bronchodilation in an individual in whom it is indicated; the required therapeutic amount varies from individual to individual and from indication to indication, but it is easily determined by one skilled in the field without undue experimentation. Indications for producing bronchodilation include a variety of respiratory diseases in which the bronchial tree is constricted and which respond to bronchodilation, notably intrinsic or extrinsic asthma and emphysema.

Means for administration of 1-decarboxy-1-hydroxymethyl-$PGE_1$ include parenteral, inhalational, or other conventional means. Administration of the compound by inhalation is a preferred mode.

Compositions of 1-decarboxy-1-hydroxymethyl-$PGE_1$ for administration by inhalation comprise the compound and a pharmaceutically acceptable vehicle. The latter depends on delivery means such as a standard nebulizer or a pressurized container. Thus compositions for delivery by a nebulizer comprise 1-decarboxy-1-hydroxymethyl-$PGE_1$ in a suitable solvent such as water, an aqueous alcohol solution, or an alcohol. The compositions for delivery from a pressurized container comprise a solution or suspension of 1-decarboxy-1-hydroxymethyl-$PGE_1$ in a conventional liquefied propellant. The compositions also comprise the compound and a solid diluent for delivery for administration from a powder inhalation device. Such compositions are easily prepared by those skilled in the art according to well known procedures utilized in the pharmaceutical sciences.

In addition to 1-decarboxy-1-hydroxymethyl-$PGE_1$ the compositions may contain other active bronchodilating agents such as isoprenaline, orciprenaline, or salbutannol.

Use of 1-decarboxy-1-hydroxymethyl-$PGE_1$ to elicit bronchodilation affords advantages over use of $PGE_1$. Unlike the latter, 1-decarboxy-1-hydroxymethyl-$PGE_1$ does not cause tracheal-bronchial irritation at equivalent dosages. Further, as the following examples indicate, 1-decarboxy-1-hydroxymethyl-$PGE_1$: is 24-times more potent than $PGE_1$ in relaxing guinea pig tracheal tissue in vitro; is 4-times more effective than $PGE_1$ at 0.001 $\mu$g/ml in inhibition of histamine-induced bronchoconstriction in guinea pig in vivo; and inhibits the effects of $PGE_1$ in guinea pig ileum tissue in vitro.

EXAMPLE 1

Comparative Relaxation of Guinea Pig Tracheal Tissue In Vitro by 1-Decarboxy-1-Hydroxymethyl-$PGE_1$ and $PGE_1$ Male guinea pigs weighing 200–500 g were killed by a blow on the head. A 20 mm length of trachea was dissected from each of the animals, transferred to a petri dish containing Krebs' solution aerated with 95% $O_2$ and 5% $CO_2$ at 37° C, and cut longitudinally opposite the tracheal muscle. The tissue was then cut transversely three quarters of the distance across; a second cut in the opposite direction again three quarters of the distance across the tissue was made, and the procedure was continued for the whole tissue. The ends of the trachea were pulled to form a zig-zag shaped strip. The tracheal strips used in the experiment were approximately 30 mm when extended under 0.25–0.5 g load in a tissue bath. Cotton thread was tied to one end of the tissues, and linen thread to the other. The tissues were attached via the linen thread to a glass hook in a 5 ml isolated tissue bath containing Krebs' solution at 37° C aerated with a mixture of 95% $O_2$ and 5% $CO_2$. The opposite ends were attached via cotton thread to an isotonic transducer. The load on the transducer lever was small, usually 0.3 g, with a range of 0.25–0.5 g; and the magnification high, 80-fold using an appropriate twin-channel pen recorder. A minimum of thirty minutes was allowed before applying a drug to the tissues. Drugs were then applied (in volumes of 0.5 ml) at thirty minute intervals, being in contact with the tissue for five minutes followed by an overflow washout time of twenty seconds.

Table A provides data on the relaxation of the tracheal tissue by 1-decarboxy-1-hydroxymethyl-$PGE_1$.

Table B contains comparative data for 1-decarboxy-1-hydroxymethyl-$PGE_1$ and $PGE_1$ obtained utilizing the above assay; the former compound is clearly more effective at equivalent concentrations.

Table A

Relaxation of Guinea Pig Tracheal Tissue by
1-Decarboxy-1-Hydroxymethyl-$PGE_1$ In Vitro

| Concentration in μg/ml | Relaxation (×80) in mm | | |
|---|---|---|---|
| | 1st Tissue | 2nd Tissue | Mean Response |
| 0.01 | 30 | 30 | 30 |
| 0.10 | 113 | 93 | 104 |
| 1.00 | 153 | 173 | 163 |
| 10.00 | 146 | 199 | 172 |

Table B

Comparison of Relaxation of Guinea Pig Tracheal Tissue
by $PGE_1$ and by 1-Decarboxy-1-Hydroxymethyl-$PGE_1$

| Concentration of Test Compound in μg/ml | Relaxation (×80) mm (± S.E.)* | |
|---|---|---|
| | $PGE_1$ | 1-Decarboxy-1-Hydroxymethyl-$PGE_1$ |
| 0.001 | 0 | 24 (18) |
| 0.010 | 24 (1) | 59 (30) |
| 0.100 | 46 (19) | 79 (21) |
| 1.000 | 75 (17) | 104 (14) |
| 10.000 | 75 (65) | 105 (35) |

*± S.E. is Standard Error

EXAMPLE 2

Inhibition of Histamine-Induced Bronchoconstriction In The Anesthetized Guinea Pig In Vivo by Intravenous Administration of $PGE_1$ or of 1-Decarboxy-1-Hydroxymethyl-$PGE_1$ Male albino guinea pigs (400–600 g; Dunkin-Hartley Strain) were anesthetized with pentobarbitone sodium (60 mg/kg intraperitoneally).

Trachea, external jugular vein and carotid artery were cannulated for recording ventilation, intravenous administration of drugs, and blood pressure respectively. The animals were artificially respired throughout the experiment. Electrocardiograms were also recorded. Respiratory flow was charted on a twin-channel recorder fixed to an SE differential pressure transducer.

Histamine was administered intravenously at 5 minute intervals. The test drug was administered intravenously 15 seconds prior to histamine in order to inhibit bronchoconstriction.

Comparative data for $PGE_1$ and for 1-decarboxy-1-hydroxymethyl-$PGE_1$ obtained from the above experiment are presented in Table C.

Table C

Inhibition of Histamine-Induced Bronchoconstriction
in the Anesthetized Guinea Pig In Vivo by
Intravenous Administration of $PGE_1$ or of
1-Decarboxy-1-Hydroxymethyl-$PGE_1$

| | Dose in ng/kg I.V., Inhibiting Bronchoconstriction by 50% ($ID_{50}$) | | |
|---|---|---|---|
| Experiment No. | A. $ID_{50}$ for $PGE_1$ | B. $ID_{50}$ for 1-Decarboxy-1-Hydroxymethyl-$PGE_1$ | Ratio of $ID_{50}$ Values (A/B) |
| 1 | 603 | 529 | 1.14 |
| 2 | 966 | 733 | 1.25 |
| 3 | 263 | 225 | 1.17 |
| 4 | 864 | 756 | 1.14 |
| 5 | 202 | 193 | 1.05 |
| Mean | 579 | 495 | 1.17 |

EXAMPLE 3

Inhibition of Intravenous Histamine-Induced Bronchoconstriction In The Anesthetized Guinea Pig By Inhalational Administration of $PGE_1$ and of 1-Decarboxy-1-Hydroxymethyl-$PGE_1$ Details of the procedure of this example are the same as those in preceding Example 2 with the exception that the test compounds were delivered in aerosol form into the trachea of the test animals.

Table D provides comparative data for each compound tested.

Table D

Inhibition of Intravenously Histamine-Induced
Bronchoconstriction in the Anesthetized Guinea Pig
In Vivo by Inhalational Administration of $PGE_1$
or of 1-Decarboxy-1-Hydroxymethyl-$PGE_1$

| Concentration in μg/ml of Test Compound in Stock Solution Aerosolized | Precent Inhibition of Histamine-Induced Bronchoconstriction | |
|---|---|---|
| | $PGE_1$ | 1-Decarboxy-1-Hydroxymethyl-$PGE_1$ |
| 0.001 | 6 | 24 |

EXAMPLE 4

Delay by Inhaled 1-Decarboxy-1-Hydroxymethyl-$PGE_1$ or by $PGE_1$ of Convulsions Induced by Inhaled Histamine in Conscious Guinea Pigs Conscious male albino guinea pigs (Dunkin-Hartley strain) weighing 200–300 g were placed (singly) in a 5-liter transparent chamber for 1 minute and subjected to an aerosol of vehicle or test drug in solution, plus histamine (1% w/v).

The time from the beginning of the administration of the aerosol to the start of the first convulsion (when the guinea pig is immediately removed from the aerosol) is the pre-convulsion time. Twenty-four hours later the general procedure was repeated. Guinea pigs treated with the test drug on the first day were treated with vehicle on the second day and vice versa in a cross-over design. Maximum time allowed in the aerosol was 10 minutes. An ultrasonic humidifier was used to produce the aerosol.

Table E provides data from two experiments demonstrating the ability of 1-decarboxy-1-hydroxymethyl-$PGE_1$ or of $PGE_1$ to delay convulsions induced by inhaled histamine in guinea pigs.

Significant prolongation of preconvulsion time was obtained at concentrations of 1-decarboxy-1-hydroxymethyl-PGE$_1$ ranging from 0.01 to 25 μg/ml in the stock solution, whereas comparable tests gave significant prolongation only between the concentration range of 0.5–2.5 μg/ml.

EXAMPLE 5

Antagonism of 1-Decarboxy-1-Hydroxymethyl-PGE$_1$ to PGE$_1$ in the Guinea Pig Ileum In Vitro The degree and specificity of antagonism of 1-decarboxy-1-hydroxymethyl-PGE$_1$ to the smooth muscle stimulant effects of PGE$_1$ were assessed in segments of terminal guinea pig ileum. Preparations were placed in tissue chambers filled with Ringer-Tyrode solution at 37° C, bubbled with a mixture of 95% O$_2$ and 5% CO$_2$, and arranged for isometric recording with force displacement transducers. The segments were stretched to an initial tension of 1 g, and responses to a test concentration of acetylcholine (0.1 mcg/ml) were obtained every 5 minutes until two similar responses were observed (usually after four administrations). Responses to PGE$_1$ Table E Delay by Inhaled 1-Decarboxy-1-Hydroxymethyl-PGE$_1$ or PGE$_1$ of Convulsions Induced by Inhaled Histamine in Conscious Guinea Pigs

| Expt. No. | Concentration in μg/ml of 1-Decarboxy-1-Hydroxy-methyl-PGE$_1$ in Stock Solution Aerosolized | Prolongation of Preconvulsion Time (Seconds) | P Value | Expt. No. | Concentration in μg/ml of PGE$_1$ in a Stock Solution Aerosolized | Prolongation of Preconvulsion Time (Seconds) | P Value |
|---|---|---|---|---|---|---|---|
| 1A | 0.10 | 99 | <0.02 | | 0.50 | 77 | <0.1 |
| | 0.50 | 140 | <0.001 | | 2.50 | 225 | <0.001 |
| | 2.50 | 141 | <0.01 | 1B | 5.00 | 139 | N.S. |
| | 10.00 | 181 | <0.02 | | 10.00 | 267 | N.S. |
| | 0.01 | 54 | <0.01 | | 0.10 | 495 | N.S. |
| | 0.10 | 41 | <0.05 | | 0.50 | 274 | <0.01 |
| 2A | 1.00 | 108 | <0.02 | 2B | 1.00 | 294 | <0.01 |
| | 10.00 | 198 | <0.02 | | | | |
| | 25.00 | 302 | <0.001 | | 5.00 | 664 | N.S. |

N.S.: Not significant at P 0.05

(0.1 mcg/ml) were obtained and recorded at 5 minute intervals before and after 100 seconds of incubation with 0.1 and 1.0 mcg/ml of 1-decarboxy-1-hydroxymethyl-PGE$_1$. Any direct contractile effect of the test compound was recorded and evaluated in terms of mean values in grams of tension developed at each concentration. Responses to the agonist observed after incubation with the test compound were expressed as percent of control responses. All drugs were administered in a volume of 0.1 ml.

Table F provides data obtained from the procedure using PGE$_1$ and 1-decarboxy-1-hydroxymethyl-PGE$_1$. At a concentration of 0.1 mcg/ml, 1-decarboxy-1-hydroxymethyl-PGE$_1$ blocked 38% of the effect of PGE$_1$ and at a concentration of 1.0 mcg/ml, 100% of the effects of PGE$_1$. 1-Decarboxy-1-hydroxymethyl-PGE$_1$ has no effect on the tissue at the tested concentrations. That suggests that 1-decarboxy-1-hydroxymethyl-PGE$_1$ is less likely to cause gastrointestinal side-effects than does PGE$_1$.

Table F

Antagonism by 1-Decarboxy-1-Hydroxymethyl-PGE$_1$ to Effects of PGE$_1$ on the Guinea Pig Ileum In Vivo

| Concentration of 1-Decarboxy-1-Hydroxymethyl-PGE$_1$ in mcg/ml | Direct Effect, gm tension | %-Blockade of Tissue Response to 0.1 mcg/ml of PGE$_1$ |
|---|---|---|
| 0.1 | 0.0 | 38 |
| 1.0 | 0.0 | 100 |

EXAMPLE 6

Low Incidence of Tracheobronchial Irritancy (Coughing) in Cats after Inhalation of 1-Decarboxy-1-Hydroxymethyl-PGE$_1$ Compared with PGE$_1$ in Vivo A male and a female adult conscious cat were each challenged at 2–3 day intervals by aerosolized solutions containing either 1-decarboxy-1-hydroxymethyl-PGE$_1$ or PGE$_1$ dissolved in ethanol (0.001–10% v/v) in 0.9% w/v sodium chloride solution. A solution containing 10% v/v in 0.9% w/v sodium chloride did not cause coughing in any of the 14 experiments carried out. A test drug was given at concentrations from 0.01 μg/ml (up to 100 μg/ml) at two hour intervals exposing each cat for up to 10 minutes each time. If coughing occurred no further challenge was given that day. Two to three days later the other test substance was given. The aerosol was delivered from an ultrasonic nebulizer via rubber tubing connected to a face mask fitted to the cat. The animal was mildly restrained. Coughing was noted by an observer and also monitored by a microphone connected to a tape recorder.

Table G shows clearly that 1-decarboxy-1-hydroxymethyl-PGE$_1$ produces a much lower incidence of tracheobronchial irritancy than does PGE$_1$ at equivalent concentrations in the cat. This suggests that at equivalent therapeutic dosage 1-decarboxy-1-hydroxymethyl-PGE$_1$ is superior to PGE$_1$.

Table G

Effect of PGE$_1$ or 1-Decarboxy-1-Hydroxymethyl-PGE$_1$ Given by Inhalation in the Conscious Cat.

| Test Compound | Concentration of Test Compound in μg/ml of Stock Solution Aerosolized | Incidence of Coughing in a Male (M) and Female (F) Cat | |
|---|---|---|---|
| | | M | F |
| 1-Decaroxy-1- | 0.10 | 0/3 | 0/3 |
| | 0.10 | 0/3 | 0/3 |

Table G-continued

Effect of PGE$_1$ or 1-Decarboxy-1-Hydroxymethyl-PGE$_1$
Given by Inhalation in the Conscious Cat.

| Test Compound | Concentration of Test Compound in μg/ml of Stock Solution Aerosolized | Incidence of Coughing in a Male (M) and Female (F) Cat | |
|---|---|---|---|
| | | M | F |
| hydroxy-methyl-PGE$_1$ | 1.00 | 0/3 | 1/3 |
| | 10.00 | 0/3 | |
| | 100.00 | 0/2 | |
| | 0.01 | 0/4 | 0/4 |
| | 0.10 | 0/4 | 3/4 |
| PGE$_1$ | 1.00 | 0/4 | |
| | 10.00 | 3/4 | |

What is claimed is:

1. A therapeutic method of causing bronchodilation in an individual in whom that therapy is indicated comprising:
    administering to the individual a therapeutically effective amount of 15(S)-1,11α,15α-trihydroxy-9-oxo-13-trans-prostene.

2. The method as in claim 1 wherein the 15(S)-1,11α,15α-trihydroxy-9-oxo-13-trans-prostene is administered by inhalation.

3. The method as in claim 1, wherein the 15(S)-1,11α,15α-trihydroxy-9-oxo-13-trans-prostene is administered intravenously.

* * * * *

UNITED STATES PATENT OFFICE
CERTIFICATE OF CORRECTION

PATENT NO. : 4,022,912
DATED : May 10, 1977
INVENTOR(S) : Phillip J. Gardiner & Cyril Schneider It is certified that error appears in the above-identified patent and that said Letters Patent are hereby corrected as shown below:

In column 1, lines 58-66, delete structure (I) and instead insert --

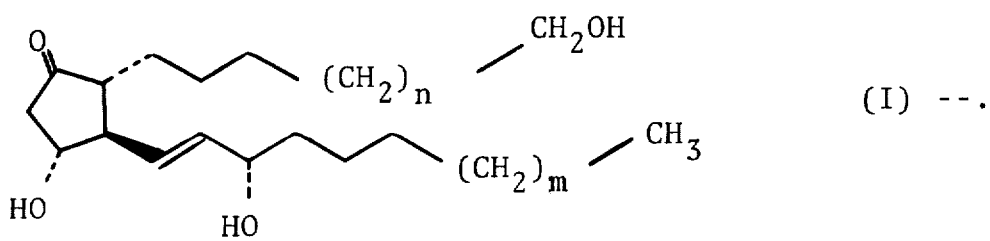   (I) --.

In column 2, lines 3-10, delete structure (II) and instead insert --

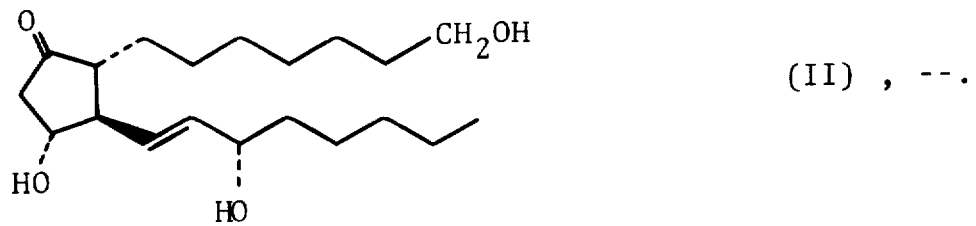   (II) , --.

UNITED STATES PATENT OFFICE
CERTIFICATE OF CORRECTION

PATENT NO. : 4,022,912
DATED : May 10, 1977
INVENTOR(S) : Phillip J. Gardiner & Cyril Schneider It is certified that error appears in the above-identified patent and that said Letters Patent are hereby corrected as shown below:

In column 2, lines 15-50, delete entire sequence and instead insert --

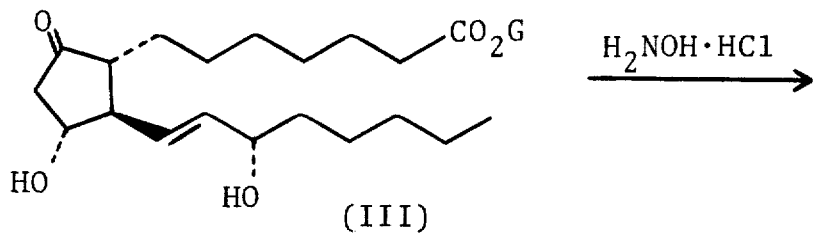

(III)

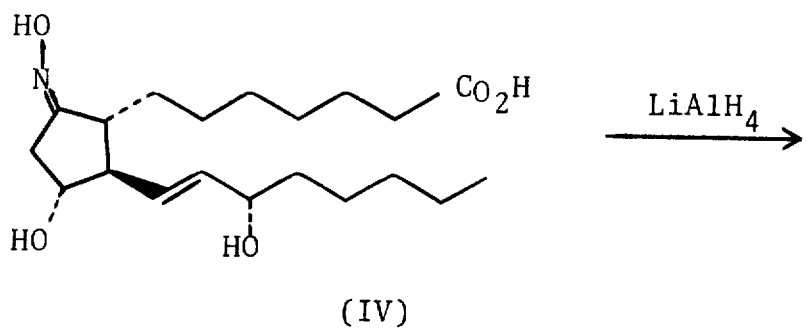

(IV)

UNITED STATES PATENT OFFICE
CERTIFICATE OF CORRECTION

PATENT NO. : 4,022,912
DATED : May 10, 1977
INVENTOR(S) : Phillip J. Gardiner & Cyril Schneider It is certified that error appears in the above-identified patent and that said Letters Patent are hereby corrected as shown below:

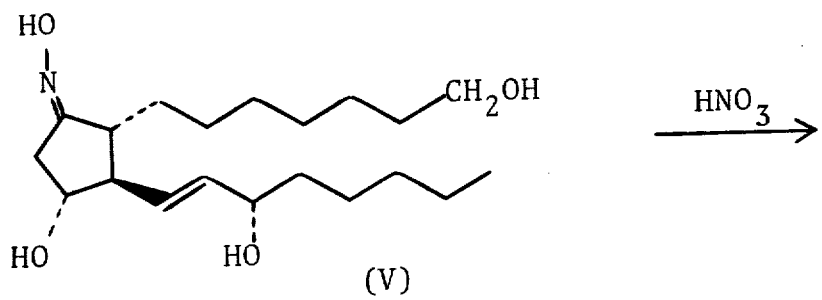

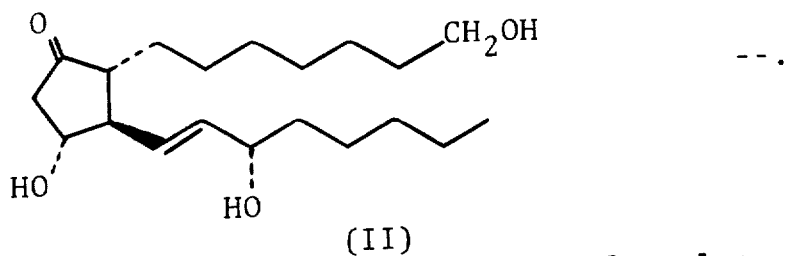

Signed and Sealed this thirtieth Day of August 1977

[SEAL]

Attest:

RUTH C. MASON
Attesting Officer

C. MARSHALL DANN
Commissioner of Patents and Trademarks